United States Patent [19]

Nakamura et al.

[11] Patent Number: 6,057,118

[45] Date of Patent: May 2, 2000

[54] METHOD FOR QUANTITATIVELY DETERMINING LDL CHOLESTEROLS

[75] Inventors: Mitsuhiro Nakamura; Kazuo Nakanishi; Koichi Hino; Mitsuhisa Manabe, all of Ryugasaki, Japan

[73] Assignee: Daiichi Pure Chemicals Co., Ltd., Tokyo, Japan

[21] Appl. No.: 09/147,296

[22] PCT Filed: Apr. 10, 1997

[86] PCT No.: PCT/JP97/01232

§ 371 Date: Nov. 23, 1998

§ 102(e) Date: Nov. 23, 1998

[87] PCT Pub. No.: WO97/45553

PCT Pub. Date: Dec. 4, 1997

[30] Foreign Application Priority Data

May 29, 1996 [JP] Japan ..................................... 8-134727

[51] Int. Cl.⁷ ............................... C12Q 1/60; C12Q 1/44; C12Q 1/26; C12Q 1/32; G01N 33/92

[52] U.S. Cl. ................................. 435/11; 435/19; 435/25; 435/26; 436/71

[58] Field of Search .................................. 435/11, 19, 28, 435/25, 26; 436/71; 564/505

[56] References Cited

U.S. PATENT DOCUMENTS

| | | | |
|---|---|---|---|
| 4,544,630 | 10/1985 | Ziegenhorn et al. | 435/11 |
| 4,840,942 | 6/1989 | Iwasaki et al. | 514/120 |
| 4,851,335 | 7/1989 | Kerscher et al. | 435/11 |
| 4,892,815 | 1/1990 | Kerscher et al. | 435/7 |
| 5,286,626 | 2/1994 | Law et al. | 435/19 |
| 5,773,304 | 6/1998 | Hino et al. | 436/174 |
| 5,807,696 | 9/1998 | Miyauchi et al. | 435/11 |

FOREIGN PATENT DOCUMENTS 07301636  11/1995  Japan ............................. G01N 33/92

*Primary Examiner*—Michael P. Woodward
*Assistant Examiner*—Marjorie A. Moran
*Attorney, Agent, or Firm*—Oblon, Spivak, McClelland, Maier & Neustadt, P.C.

[57] ABSTRACT

A method for quantitatively determining LDL cholesterol, including the steps of adding to serum a surfactant selected from among polyoxyethylenealkylene phenyl ethers and polyoxyethylenealkylene tribenzylphenyl ethers and a cholesterol-assaying enzyme reagent so as to preferentially react cholestrols in high density- and very low density-cholesterols among lipoproteins, and subsequently determining the amount of cholesterol that reacts thereafter. This method can eliminate the necessity for pretreatments such as centrifugation and electrophoresis, enables the quantitative determination to be conducted in an efficient, simple manner, and can be applied to various automatic analyzers.

12 Claims, 3 Drawing Sheets

METHOD FOR QUANTITATIVELY DETERMINING LDL CHOLESTEROLS

TECHNICAL FIELD

The present invention relates to a method for quantitatively and fractionally determining LDL (Low Density Lipoprotein) cholesterol and cholesterol in lipoproteins other than LDL in an efficient, simple manner which requires a small amount of samples and requires no treatment for separation, such as centrifugation or electrophoresis.

BACKGROUND ART

Lipids such as cholesterols bind to apoprotein in serum to form lipoprotein. Lipoprotein is typically classified as chylomicron, very low density lipoprotein (VLDL), low density lipoprotein (LDL), high density lipoprotein (HDL), etc. according to physical properties. Among them, LDL is known to be a casual substance inducing arteriosclerosis.

Several epidemiological studies have clarified that the LDL cholesterol level is strongly correlated to onset frequency of arteriosclerotic disease. Therefore, realization of measurement of LDL cholesterol through a simple routine method might be very useful clinically.

With regard to conventional methods for measuring LDL cholesterol, there have been known, for example, a method in which LDL is separated from other lipoproteins by ultracentrifugation to measure cholesterol and a method in which lipid is stained after separation through electrophoresis so as to measure the intensity of developed color. However, most of these methods are not used routinely, due to their intricate operations and limitations in handling a number of specimens. There is also known a method in which a carrier is sensitized with an antibody which binds a lipoprotein other than LDL, then mixed with a sample, and a fraction not bound to he carrier is fractionated to measure cholesterols therein. Although this method is more suited for routine assay as compared with the previous two methods, the assay procedure involves manual steps, which makes automation of the assay procedures difficult. Thus, the method is still unsuited for handling a large number of specimens.

Meanwhile, with regard to a method for quantitatively and fractionally determining lipoproteins in a sample without using means for separation such as ultracentrifugation or electrophoresis, there has been known a method in which, upon fractional determination of cholesterols in HDL and other lipoproteins (i.e., chylomicron, VLDL, and LDL), reactivity of enzymes employed (typically cholesterol oxidase and cholesterol esterase) is controlled to induce exclusively HDL cholesterol to enzyme reaction. For example. Japanese Patent Application Laid-Open (kokai) No. 7-301636 discloses a method for exclusively measuring HDL cholesterol by use of a surfactant and a sugar compound, and Japanese Patent Application Laid-Open (kokai) No. 6-242110 discloses a method for exclusively measuring cholesterol in a target lipoprotein by agglutinating lipoproteins other than the lipoprotein to be measured so as to control reactivity with an enzyme. These methods are significantly useful in view of applicability thereof to automatic analyzers which realize automation of all steps. However, these methods have limitations in that they can quantitatively determine only HDL fractionated from lipoproteins other than HDL, and have no further ability to determine LDL quantitatively and fractionally from a mixture of VLDL and chylomicron. Therefore, these methods cannot meet an objective to measure LDL cholesterol without using separation means.

Japanese Patent Application Laid-Open (kokai) No. 7-280812 discloses a method for determining LDL cholesterol comprising the steps of agglutinating LDL; removing cholesterols in other lipoproteins by a system which differs from a system for determining LDL; dissolving the agglutination of LDL; and reacting the LDL cholesterol. However, similar to the method described in the above two publications, Japanese Patent Application Laid-Open (kokai) No. 7-280812 proposes no resolution to quantitative and fractional determination of LDL and VLDL and/or chylomicron, which is absolutely essential for determining LDL cholesterol. There is also a problem with this method; it cannot be applied to commonly-used automatic analyzers due to a large number of steps required to the assay, making this method of very limited use.

Thus, with conventional techniques, LDL cholesterol can never be assayed effectively without performance of an operation for separation, and, moreover, there has been no information indicating possibility of the above measurement.

Accordingly, an object of the present invention is to provide a method for qualitatively and fractionally determining LDL cholesterol efficiently in a simple manner while eliminating necessity for pretreatments such as centrifugation or electrophoresis and which can be applied to a variety of automatic analyzers.

DISCLOSURE OF THE INVENTION

In view of the foregoing, the present inventors have conduced earnest studies, and have found that reaction with a cholesterol-assaying enzyme reagent performed in the presence of a specific surfactant which dissolves lipoproteins accelerates reaction of HDL cholesterol and VLDL cholesterol and remarkably retards reaction of LDL cholesterol; that reaction of HDL cholesterol and VLDL cholesterol are terminated prior to reaction of LDL cholesterol; and that LDL cholesterol can be measured quantitatively and fractionally by appropriate selection of a point of measurement, allowing for application to automated analyzers. The present invention was accomplished based on these findings.

Accordingly, the present invention provides a method for quantitatively determining LDL cholesterol, comprising the steps of adding to serum a surfactant selected from among polyoxyethylenealkylene phenyl ethers and polyoxyethylenealkylene tribenzylphenyl ethers and a cholesterol-assaying enzyme reagent, to thereby induce preferential reactions of cholesterols in high density- and very low density-lipoproteins among lipoproteins, and subsequently determining the amount of cholesterol which reacts thereafter.

The present invention also provides a method for quantitatively determining LDL cholesterol, characterized by comprising the steps of adding to serum a surfactant selected from among polyoxyethylenealkylene phenyl ethers and poloxyethylenealkylene tribenzylphenyl ethers, a substance exhibiting stronger bonding affinity to VLDL than to LDL, and a cholesterol-assaying enzyme reagent, to thereby induce preferential reactions of cholesterols in high density- and very low density-lipoproteins among lipoproteins, and subsequently determining the amount of cholesterol which reacts thereafter.

Furthermore, the present invention provides a kit for quantitatively determining LDL cholesterol, comprising a cholesterol-assaying enzyme reagent and a surfactant selected from among polyoxyethylenealkylene phenyl ethers and polyoxyethylenealkylene tribenzylphenyl ethers.

Furthermore, the present invention provides a kit for quantitatively determining LDL cholesterol as described above, further comprising a substance which exhibits stronger bonding affinity to VLDL than to LDL.

BEST MODES FOR CARRYING OUT THE INVENTION

Figure 1:
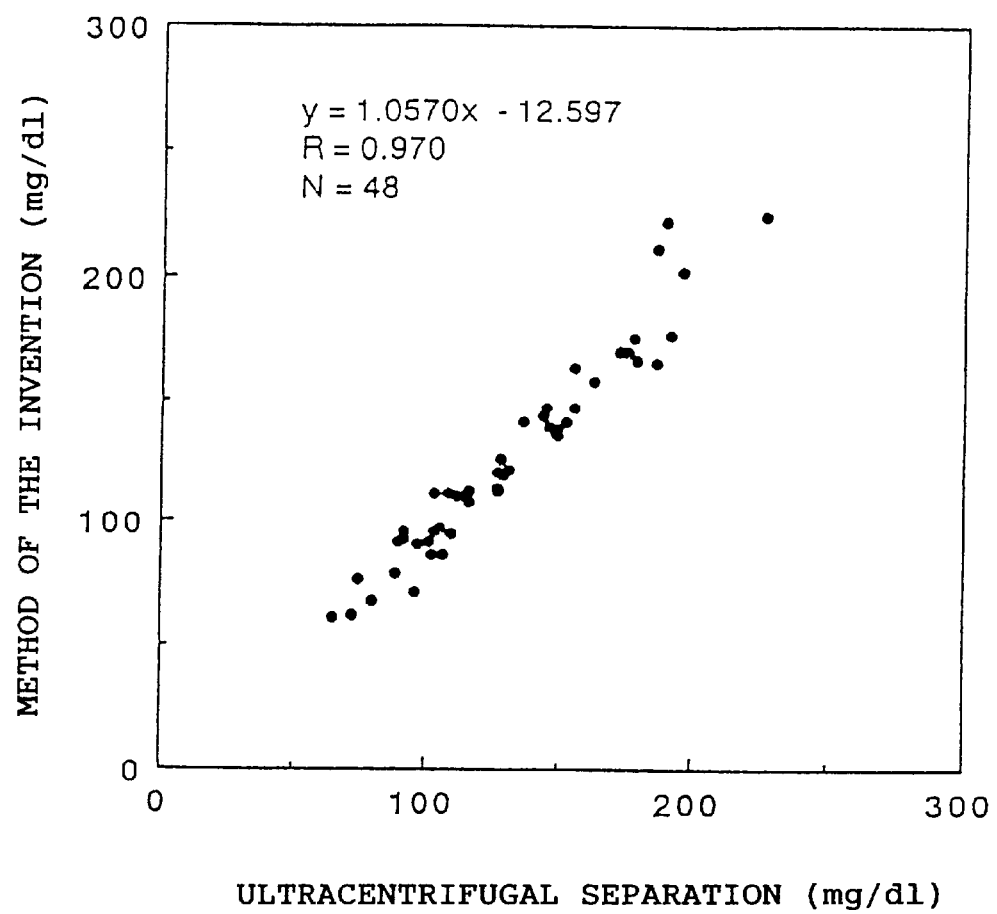
FIG. 1 shows correlation of measurements of LDL cholesterol obtained in Example 1 through a method of the present invention and measurements of LDL cholesterol obtained through ultracentrifugation.

The surfactants which are used in the present invention are selected from among polyoxyethylenealkylene phenyl ethers and polyoxyethylenealkylene tribenzylphenyl ethers and dissolve lipoproteins. Examples of the former ethers include Emulgen A-60 (Product of Kao Corporation) and examples of the latter ethers include Emulgen B66 (Product of Kao Corporation). The surfactants may be used singly or in combination of two or more species. The amount of use depends on the compound and is not particularly limited. Under normal conditions, the surfactants are preferably used at a concentration of 0.01–2 wt. % so as to obtain a sensitivity that permits detection of LDL cholesterol within a desired assay time, which differs in accordance with the analytical apparatus to which a reagent is applied.

The method for assaying cholesterol according to the present invention is preferably practiced in the presence of a substance exhibiting stronger bonding affinity to VLDL than to LDL. Particularly, when the specimen is chylomicron-containing serum, addition of the above substance provides excellent assay results. Examples of such substances include polyanions and substances forming a divalent metal salt. Specific examples of the polyanions include phosphotungstic acid and salts thereof, dextran sulfate, and heparin; and more specific examples of the above substances include divalent metal chlorides such as $MgCl_2$, $CaCl_2$, $MnCl_2$, or $NiCl_2$ or hydrates thereof. These substances may be used singly or in combination of two or more species. The amount of use depends on the compound and is not particularly limited. Preferably, polyanions are used in an amount of 0.002–10 wt. % and the substances forming divalent metal ions are used in an amount of 0.01–1 wt. %, both in terms of a terminal concentration in reaction.

A surfactant and a substance exhibiting stronger bonding affinity to VLDL than to LDL are added to serum serving as a specimen and may be added separately or in the form of a mixture. Briefly, the former, the latter, and a cholesterol-assaying enzyme reagent may be added separately; either of the former and the latter and a mixture of the counterpart and a cholesterol-assaying enzyme reagent may be added separately; or a mixture of the three components may be added as a reagent.

Any known enzymatic assay methods may be used for assaying cholesterols. Examples of the methods include a method employing a combination of cholesterol esterase and cholesterol oxidase as an enzyme reagent, as well as a method employing a combination of cholesterol esterase and cholesterol dehydrogenase as an enzyme reagant. Of these, a method employing a combination of cholesterol esterase and cholesterol oxidase is preferred. No particular limitation is imposed on the method for finally detecting cholesterols following addition of these cholesterol-assaying enzyme reagants, and examples thereof include an absorptiometric analysis employing a further combination of peroxidase and a chromogen and direct detection of a coenzyme of hydrogen peroxide.

In order to perform an LDL cholesterol assay, the amount of relevant reaction is determined after termination of reactions of cholesterols in lipoproteins other than LDL. There may be employed a method in which reaction of cholesterols in lipoproteins other than LDL is substantially completed after allowing the reaction to proceed for a specific time, and a reaction which proceeds thereafter is kinetically monitored. Alternatively, there may be employed a method in which an additional reaction-accelerating agent is further added so as to accelerate reaction of LDL; the reaction that has caused therefrom is measured through a reaction endpoint method; and the value is adjusted by use of a blank value (2-points method). With regard to the reaction-accelerating agents which may be used in the 2-points method include the same surfactants that are used in reaction of cholesterols in lipoproteins other than LDL in a higher concentration and another kind of surfactant. In the 2-points method, cholesterols may be introduced into another reaction system isolated from a system for determining LDL to exclusively detect reaction of LDL cholesterol during reaction of cholesterols in lipoproteins other than LDL.

Examples of other lipoproteins contained in serum include chylomicron, which typically appears exclusively after ingestion of food. Chylomicron has approximately the same reactivity as that of VLDL. Therefore, reactivity of chylomicron is also accelerated in a manner similar to the case of VLDL by addition of polyanions, a substance which forms divalent metal ions, etc. and reaction of chylomicron is also completed when the reaction of VLDL is completed. Thus, LDL cholesterol may be determined quantitatively and fracitonally through measurement of the reaction amount of cholesterols thereafter.

EXAMPLES

The present invention will next be described by way of examples, which should not be construed as limiting the invention thereto.

Example 1

Normal-lipid serum specimens were assayed for LDL cholesterol through a method of the present invention by use of a Hitachi model 7070 automatic analyzer, and the measurements were compared with those obtained through ultracentrifugation. The results are shown in FIG. 1.

Briefly, to a specimen (45 µl), a reagent (300 µl) containing sodium phosphotungstate (0.02 wt. %) and $MgCl_2.6H_2O$ (0.2 wt. %) was added. Approximately five minutes later, there was added a cholesterol-assaying reagent (100 µl) containing Emulgen A-60 (product of Kao Corporation) (0.5 wt. %), cholesterol esterase (1 U/ml), cholesterol oxidase (1 U/ml), peroxidase (1 U/ml), 4-aminoantipyrine (0.005 wt. %), and N,N-dimethyl-m-toluidine (0.04 wt. %), and the changes in absorbance at 545 nm during the period of one minute to five minutes after the addition of the second reagent were measured.

For ultracentrifugation, the serum was subjected to centrifugation at 100 g for two hours by use of an ultracentrifuge, to thereby remove the upper layer. To an aliquot (1 ml) collected from the resultant lower layer, a heparin solution (40 $\mu$l; heparin=500 usp units/ml) and a 1M $MgCl_2$ solution (50 $\mu$l) were added, and the mixture was centrifuged at 5000 rpm for 30 minutes, to thereby obtain a supernatant. The solution (containing LDL and HDL) of the lower layer obtained through ultracentrifugation and the fractionated supernatant (containing HDL) obtained through addition of a solution of heparin and a solution of $MgCl_2$ were subjected to cholesterol assay, and the value obtained by subtracting the latter from the former represents the LDL cholesterol level (Reference; Paul S. Bachorik et al., Clin. Chem. 41/10, 1414–1420, 1955).

As shown in FIG. 1, the present invention provides measurements having excellent correlation to these obtained through conventional centrifugation, even though the method of the present invention requires a small amount of sample and can be carried out in a simple manner.

Example 2

A specimen that contains chylomicron-containing serum having a high triglyceride level was assayed for LDL cholesterol through a method of the present invention by use of a Hitachi model 7070 automatic analyzer, and the measurements were compared with those obtained through ultracentrifugation. The results are shown in FIG. 2.

Briefly, to a specimen (4 $\mu$l), a reagent (300 $\mu$l) containing Emulgen B66 (product of Kao Corporation) (0.5 wt. %), cholesterol esterase (0.3 U/ml), cholesterol oxidase (0.3 U/ml), peroxidase (0.3 U/ml), and 4-aminoantipyrine (0.002 wt. %) was added. Approximately five minutes later, there was added a reagent (100 $\mu$l) containing Triton X-100 (1 wt. %) and N,N-dimentyl-m-toluidine (0.04 wt. %), and the changes in absorbance were measured by subtracting the absorbance measured at 545 nm before the addition of the second reagent from the measured five minutes after the addition thereof (correction in consideration of the change in amount of the reagents).

In the ultracentrifugation step, the procedure of Example 1 was repeated.

Figure 2:
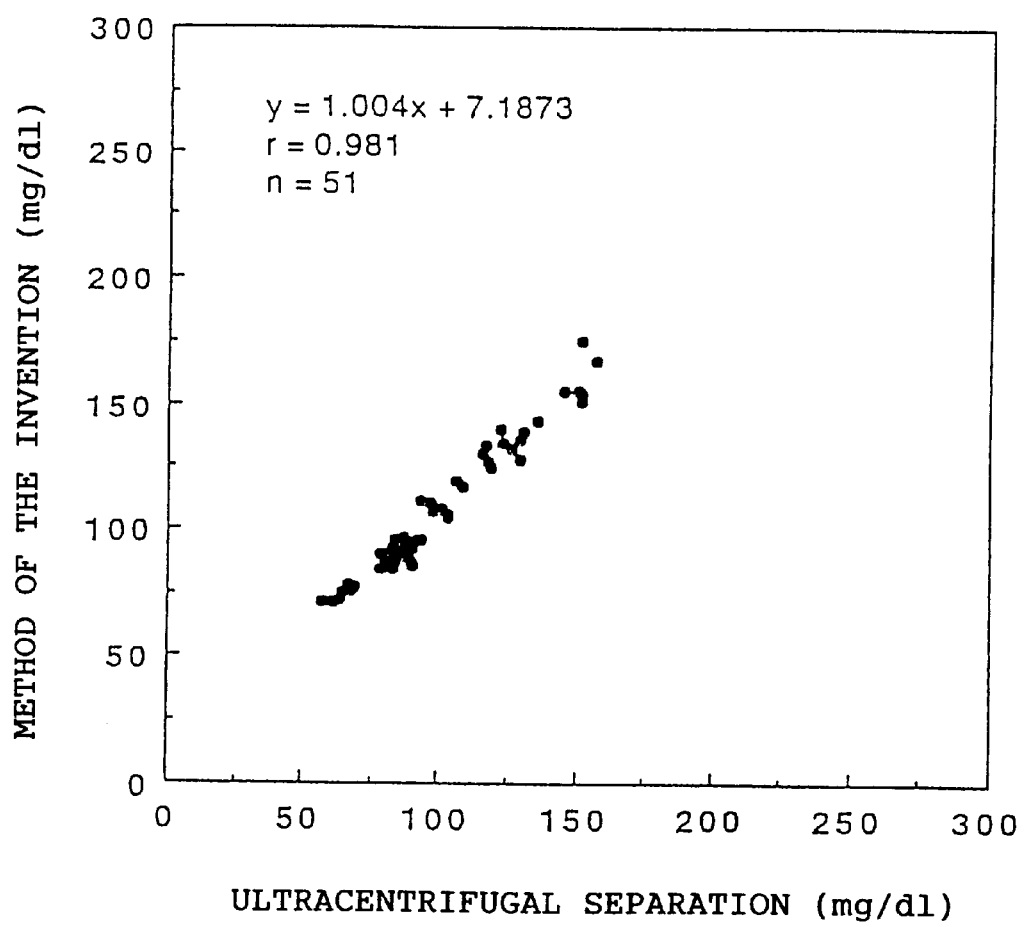
FIG. 2 shows correlation of measurements of LDL cholesterol obtained in Example 2 through a method of the present invention and measurement of LDL cholesterol obtained through ultracentrifugation.

As shown in FIG. 2, similar to the case of Example 1, in Example 2 measurements of LDL cholesterol having excellent correlation to those obtained through conventional centrifugation were obtained.

Example 3

The procedure of Example 2 was repeated by use of the same specimen and regents except that phosphotungstic acid (0.3 wt. %) was further incorporated in the first reagent, and the measurements were compared with those obtained through ultracentrifugation. The results are shown in FIG. 3.

Figure 3:
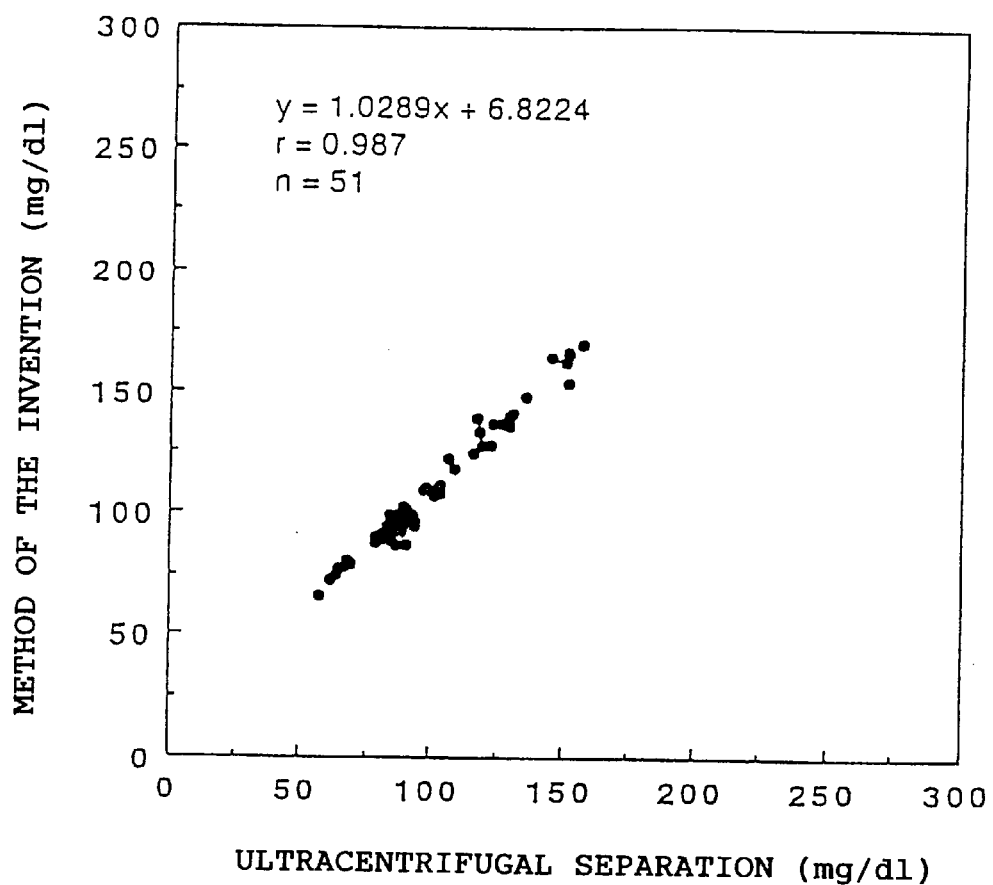
FIG. 3 shows correlation of measurements of LDL cholesterol obtained in Example 3 through a method of the present invention and measurements of LDL cholesterol obtained through ultracentrifugation.

As shown in FIG. 3, similar to the case of Example 1, in Example 3 measurements of LDL cholesterol having excellent correlation to those obtained through conventional centrifugation were obtained, even through a serum specimen containing chylomicron-containing serum was used.

INDUSTRIAL APPLICABILITY

The present invention eliminates the necessity for pretreatment such as centrifugation and electrophoresis, and enables quantitative determination of LDL cholesterol, fractional to cholesterols contained in other lipoproteins, to be performed in an efficient, simple manner, and thus can be applied to various automatic analyzers used in clinical examinations. Thus, the invention is remarkably useful in the clinical field.

We claim:

1. A method for quantitatively determining low density lipoprotein cholesterol in serum, comprising:
   (A) adding to a serum sample (1) a surfactant selected from the group consisting of polyoxyethylenealkylene phenyl ethers and polyoxyethylenealkylene tribenzylphenyl ethers and (2) a cholesterol-assaying enzyme reagent,
   wherein the surfactant accelerates reaction of the enzyme reagent with high density lipoproteins and very low density lipoproteins and retards reaction of the enzyme reagent with low density lipoproteins, and
   (B) determining the amount of cholesterol in the low-density-lipoproteins.

2. The method of claim 1, wherein in (A) a substance which has a stronger bonding affinity to very low density lipoproteins as compared to low density lipoproteins is also added to the sample.

3. The method of claim 2, wherein said substance is a polyanion or a divalent metal salt.

4. The method of claim 3, wherein the anion is phosphotoungstic acid or a salt thereof, dextran sulfate or heparin.

5. The method of claim 3, wherein the divalent metal salt is $MgCl_2$, $CaCl_2$, $MnCl_2$ or $NiCl_2$.

6. The method of claim 3, wherein the concentration of the polyanion, after addition to the sample, is 0.002 to 10 wt. %.

7. The method of claim 3, wherein the concentration of the divalent metal salt, after addition to the sample, is 0.01 to 1 wt. %.

8. The method of claim 1, wherein the concentration of the surfactant, after addition to the sample, is 0.01 to 2 wt. %.

9. The method of claim 1, wherein the cholesterol-assaying enzyme reagent comprises cholesterol esterase and cholesterol oxidase.

10. The method of claim 1, wherein the cholesterol-assaying enzyme reagent comprises cholesterol esterase and cholesterol dehydrogenase.

11. The method of claim 1, wherein the serum sample comprises chylomicron.

12. The method of claim 1, wherein the serum sample is not subjected to centrifugation or electrophoresis prior to (A).

* * * * *

UNITED STATES PATENT AND TRADEMARK OFFICE
CERTIFICATE OF CORRECTION

PATENT NO. : 6,057,118

DATED : May 2, 2000

INVENTOR(S): Mitsuhiro NAKAMURA, et al.

It is certified that an error appears in the above-identified patent and that said Letters Patent is hereby corrected as shown below:

Column 6, lines 33-34, "phosphotoungstic" should read --phosphotungstic--.

Signed and Sealed this

Third Day of April, 2001

Attest:

NICHOLAS P. GODICI

Attesting Officer

Acting Director of the United States Patent and Trademark Office